(12) United States Patent
Beutler et al.

(10) Patent No.: US 7,985,323 B2
(45) Date of Patent: Jul. 26, 2011

(54) PURIFICATION PROCESS

(75) Inventors: Ulrich Beutler, Oberwil (CH); Gerhard Penn, Oberwil (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/291,863

(22) Filed: Nov. 14, 2008

(65) Prior Publication Data

US 2009/0216047 A1    Aug. 27, 2009

Related U.S. Application Data

(63) Continuation of application No. 10/522,828, filed as application No. PCT/EP2004/009587 on Aug. 27, 2004, now abandoned.

(30) Foreign Application Priority Data

Aug. 29, 2003  (GB) .................................. 0320312.2

(51) Int. Cl.
  *B01D 3/10* (2006.01)
  *C07C 209/84* (2006.01)

(52) U.S. Cl. ............................. 203/29; 203/91; 564/497

(58) Field of Classification Search ................ 203/2, 29, 203/91; 564/387, 497
  See application file for complete search history.

(56) References Cited

U.S. PATENT DOCUMENTS

| 4,680,291 A | 7/1987 | Hamberger et al. ........... 514/183 |
| 4,755,534 A | 7/1988 | Stuetz ............................ 514/655 |
| 5,132,459 A | 7/1992 | Stuetz ............................ 564/387 |
| 5,436,354 A | 7/1995 | Nakagawa et al. | |
| 5,817,875 A | 10/1998 | Karimian et al. ............. 564/387 |
| 6,515,181 B2 | 2/2003 | Castaldi et al. | |
| 6,559,192 B2 | 5/2003 | Maccone et al. | |
| 6,569,463 B2 | 5/2003 | Patel et al. | |
| 7,288,678 B2 | 10/2007 | Tarquini et al. | |
| 2002/0123651 A1 | 9/2002 | Castaldi et al. | |

(Continued)

FOREIGN PATENT DOCUMENTS

CH   678 527    9/1991

(Continued)

OTHER PUBLICATIONS

Bharucha et al., "Double Cycloaromatization of (Z,Z)-Deca-3,7-diene-1,5,9-triyne: Evidence for the Intermediacy and Diradical Character of 2,6-Didehydronaphthalene", J. Am. Chem. Soc., vol. 114, pp. 3120-3121 (1992); HCAPLUS Abstract No. 1992:193445.
"Terbinafine", The Merck Index, (ed. S. Budavari), Whitehouse Station, NJ, p. 1564 (1996).

(Continued)

*Primary Examiner* — Virginia Manoharan
(74) *Attorney, Agent, or Firm* — Karen DeBenedictis

(57) ABSTRACT

Purification process for the preparation of the allylamine pharmaceutical terbinafine of formula I $$\text{naphthyl-CH}_2-\underset{\underset{CH_3}{|}}{N}-CH_2-\underset{(E)}{CH=CH}-C\equiv C-C(CH_3)_3 \quad I$$

in free base form or acid addition salt form, by distilling crude terbinafine base, preferably by short path distillation, e.g. at a temperature above 100° C. and reduced pressure, e.g. 0.2 mbar, and recovering the purified product in free base or acid addition salt form.

10 Claims, 1 Drawing Sheet

U.S. PATENT DOCUMENTS

| | | | |
|---|---|---|---|
| 2003/0130530 | A1 | 7/2003 | Lee et al. |
| 2006/0004230 | A1* | 1/2006 | Kaspi et al. ............... 564/373 |

FOREIGN PATENT DOCUMENTS

| | | |
|---|---|---|
| CZ | 232849 | 1/1987 |
| EP | 0 024 587 | 3/1981 |
| EP | 0 421 302 | 4/1991 |
| EP | 1 236 709 | 9/2002 |
| EP | 1 227 088 | 9/2003 |
| WO | 01/28976 | 4/2001 |

OTHER PUBLICATIONS

Beutler et al., "Die Entwicklung eines neuen, umweltgerechten Produktions prozesses für Terbinafin", CHIMIA, vol. 50, No. 4, pp. 154-156 (1996).

Jones et al., "Researches on Acetylenic Compounds. Part LXII.* The Preparation and Some Synthetical Applications of Penta-1,2,4-triene and Penta-1,2-dien-4-yne", J. Chem. Soc., pp. 341-346 (1960).

Krzeminski et al., "Phytochemistry of Berula erecta, Cicuta virosa and sium latifolium. Part 9. Essential oil of Cicuta virosa", Pharmazie, vol. 39, No. 3, p. 183 (1984); HCAPLUS Abstract No. 1984:478657.

Malinovskii et al., "Isomerization acetylenic .alpha.-olefin oxides with the triple bond in .beta. position with respect to the oxide ring", Zh. Org. Khim., vol. 3, No. 10, pp. 1792-1793 (1967); HCAPLUS Abstract No. 1968:12370.

Stütz et al., "Synthesis and Antifungal Activity of (E)-N-(6,6-Dimethyl-2-hepten-4-yny1)-N-methyl-1-naphthalenemethanamine (SF 86-327) and Related Allylamine Derivatives with Enhanced Oral Activity", J. Med. Chem., vol. 27, pp. 1539-1543 (1984).

Van Boom et al., "Chemistry of Acetylenic Ethers 85. Preparation of compounds with a 3,5-dien-1-yne system by 1,2 and 1,6-elimination of alcohols from various types of unsaturated . . .", Recl. Trav. Chem. Pays-Bas, vol. 85, No. 9-10, pp. 952-965 (1966); HCAPLUS Abstract No. 1967:46066.

Van Dongen et al., "Isomerization of Conjugated and Cumulated Systems", Recl. Trav. Chem. Pays-Bas, vol. 86, No. 11, pp. 1077-1081 (1967); HCAPLUS Abstract No. 1967:516486.

Disselnkötter et al., Grignard-Reaktionen Mit Penten(1)-in-(4) und 2-methyl-penten-(1)-in-(4); Liebig's Ann. Chem., vol. 679, pp. 26-34 (1964).

Rudisill et al., "Synthesis of Terbinafine. A Palladium Catalyzed Vinyl Iodide-Ethynylstannane Coupling", Tetrahedron Lett., vol. 29, pp. 1509-1529 (1988).

Maruzen I. et al., "The Chemical Society of Japan, Courses in Experimental Chemistry 1. Basic Operation 1", 4 Edition, pp. 161-163 and 214-226.

Tetrahedron Letters, 1996, vol. 37, pp. 57-58.

* cited by examiner

SHORT PATH DISTILLATION APPARATUS

PURIFICATION PROCESS

This is a continuation of application Ser. No. 10/522,828 filed on Jan. 31, 2005 now abandoned, which is National Stage of International Application No. PCT/EP04/09587 filed on Aug. 27, 2004, which claims benefit of Great Britain Application No. 0320312.2 filed on Aug. 29, 2003, the entire disclosures of which are hereby incorporated by reference.

The invention relates to a purification process for an allylamine pharmaceutical. It concerns a process for purifying crude terbinafine base.

Terbinafine, particularly in the form of the hydrochloride acid addition salt form, is known from e.g. EP 24587. It belongs to the class of allylamine antimycotics. It is commercially available under the trademark Lamisil®. It is effective upon both topical and oral administration, in a wide range of fungal infections. Terbinafine is particularly useful against dermatophytes, contagious fungi that invade dead tissues of the skin or its appendages such as stratum corneum, nail, and hair.

Terbinafine represents a significant advance in antifungal therapy based on its potent fungicidal action in vitro and rapid clinical efficacy in various dermatophyte infections when given orally as well as topically. It is a potent inhibitor of ergosterol biosynthesis (*Ann. NY Acad. Sci.* 544 [1988] 46-62), it blocks the action of squalene epoxidase, thus inhibiting the transformation of squalene to squalene epoxide. Although ergosterol synthesis is only partially inhibited, cell growth is completely arrested. This suggests that the fungicidal effect of terbinafine may be related to the accumulation of squalene, which at high concentrations may be toxic to the fungus. The spectrum of activity of terbinafine in vitro embraces all dermatophytes of the genera *Trichophyton, Epidermophyton* and *Microsporum*. The mean minimum inhibitory concentrations for these dermatophytes range from 0.001 µg/ml to 0.01 µg/ml (*Science* 224 [1984] 1239-1241). Terbinafine is also active in vitro against molds and dimorphic fungi, and against many pathogenic yeasts of the genera *Pityrosporum, Candida* and *Rhodotorula*.

The structure of terbinafine is as shown in formula I

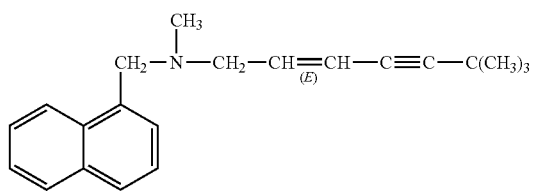

and its chemical name is i.a. (E)-N-(6,6-dimethyl-2-hepten-4-ynyl)-N-methyl-1-naphthalene methanamine.

It may be in free base form or in acid addition salt form. An acid addition salt form can be prepared from the free base form in conventional manner and vice-versa. Examples of suitable acid addition salt forms are the hydrochloride, the lactate, the ascorbate and the malate, e.g. the L-(−)-hydrogenmalate. The free base and the hydrochloride and malate salts are preferred.

As appears from formula I above, terbinafine is an allylamine compound with a triple bond conjugated with a double bond in the side chain. Terbinafine was invented many years ago (see e.g. EP 24587, Example 16), and such conjugated enyne structure was, and still is, highly unusual in the pharmaceutical field, constituting a novel structural feature in medicinal chemistry.

Both double and triple bonds are usually highly reactive. While the chemical literature does not exclude that compounds with such structure may be stable, some are unstable and may decompose upon storage or processing, such as when heat is applied, as e.g. upon distillation at elevated temperatures.

Thus it appears from e.g. E. R. H. Jones et al., *J. Chem. Soc.* (1960) 341-346 that submitting pure penta-1,2-dien-4-yne to simple distillation at its normal boiling temperature of 57°, already results in decomposition. Similarly, the (non-conjugated) 1-alken-4-yne dimer [$CH_2$=CH—$CH_2$—C=C—C($CH_3$)(OH)—]$_2$, i.e. 6,7-dimethyl-dodeca-1,1'-dien-4,8-diyn-6,7-diol (compound V in H. Disselnkötter and P. Kurtz, *Ann. Chem.* [1964] 26-34) undergoes considerable decomposition upon distillation under reduced temperature (85-90° C.) and pressure (0.05 mm Hg), as well as upon renewed distillation at 81-85° C. and 0.03 mm Hg. Further, the enediyne (Z,Z)-3,7-decadiene-1,5,9-triyne readily polymerizes when neat, and solutions thereof thermolyse at 170-190° C. to give naphthalene, while the thermolysis of the corresponding (E,Z) and (E,E) isomers gives other products or a polymer (*J. Am. Chem. Soc.* 114 [1992] 3120-3121).

Further, isomerization of conjugated enyne compounds, e.g. the ether $CH_3CH$=CH—C=C—$CH_2OC_2H_5$ to the corresponding 1,3,5-triene compound may be accompanied by considerable polymeric residue after distillation, resulting from accompanying 1,6-elimination of ethanol, while replacement of the —$OC_2H_5$ group with an amino group results in aromatization (Van-Dongen, J. et al., *Recueil Trav. Chim. Pays-Bas* 86 [1967] 1077-1081).

Additionally, overall, remarkably, it appears from e.g. the above publications that when distillation is effected at all with enyne derivatives, this is usually effected at temperatures below or slightly above 100° C., especially below about 125° C., as is to be expected with highly reactive compounds susceptible of decomposition or degradation or polymerisation, or even explosion, upon heating. This appears also for most of the alkenyne derivatives disclosed in e.g. *Recueil Trav. Chim. Pays-Bas* 85 (1966) 952-965 and *Zh. Org. Khim* 3 (1967) 1792-3 (CA 68 [1968] 12370), while the two intermediates for pheromones disclosed in Czech Author's Certificate No. 232843 (CA 106 [1984] 213632b) are purified by distillation under reduced pressure at 102-115° C. and 118-125° C., respectively.

Further, terbinafine in free base form is boiling at 140° C. at 0.3 mbar pressure, and at that temperature its thermal stability is limited: thus the following decomposition can be observed (upon analysis by gas chromatography; the area under the peak of one compound relative to the sum of all peaks is named area-%; in the case of the Z-isomer, area-% should be approximately identical with weight-%):

| Heating time (h) | By-product 1 (area-%) | Z-isomer (area-%) | Unchanged E-isomer (area-%) |
|---|---|---|---|
| 0 | 0.09 | 0.25 | 97.6 |
| 7 | 0.57 | 0.34 | 96.6 |
| 23 | 0.92 | 0.45 | 94.7 |
| 32 | 1.20 | 0.52 | 92.0 |

By-product 1 = (methyl)(naphthalen-1-ylmethyl)amine

On the other hand the product solidifies already below 43° C.

One would therefore normally refrain from effecting operations requiring substantial application of heat when working-up a chemical compound with such an unusual structure, particularly when this is associated with limited thermal stability, especially in large-scale operations, such as in the industrial production of a pharmaceutical. For example, in Example 13 of Banyu EP 0 421302 A2 describing a preparation of terbinafine, the crude mixture (free base) obtained after reaction is subjected to purification by silica gel chromatography.

However, it has been found that, surprisingly and counterintuitively, terbinafine free base may be submitted to distillation with no particularly unfavourable effect. Further, it has been found that such distillation may be effected at elevated temperature, e.g. even at a temperature significantly higher than 100° C., e.g. from about 110° C. to about 170° C., preferably from about 125° C. to about 165° C., especially about 160° C., and under correspondingly reduced pressure, e.g. 0.2 mbar at 160° C. (jacket temperature).

The yield attained thereby is normally about 95% starting from crude product.

Further, it has also been found that such distillation may even be effected using large amounts of crude terbinafine base, i.e. in an industrial setting, e.g. in the large-scale production of purified terbinafine base and acid addition salts, e.g. in amounts of at least about 5 kg, preferably at least about 50 kg, especially at least about 200 kg, e.g. from about 500 kg to about 2 tons, more preferably from about 600 kg to about 900 kg, most preferably from about 800 kg to about 900 kg, especially about 850 kg purified product in free base form per distillation batch or run.

The invention therefore concerns a novel process for the purification of terbinafine comprising subjecting crude terbinafine in free base form to distillation and recovering the resultant product in free base or acid addition salt form, hereinafter briefly named "the process of the invention".

Figure 1:
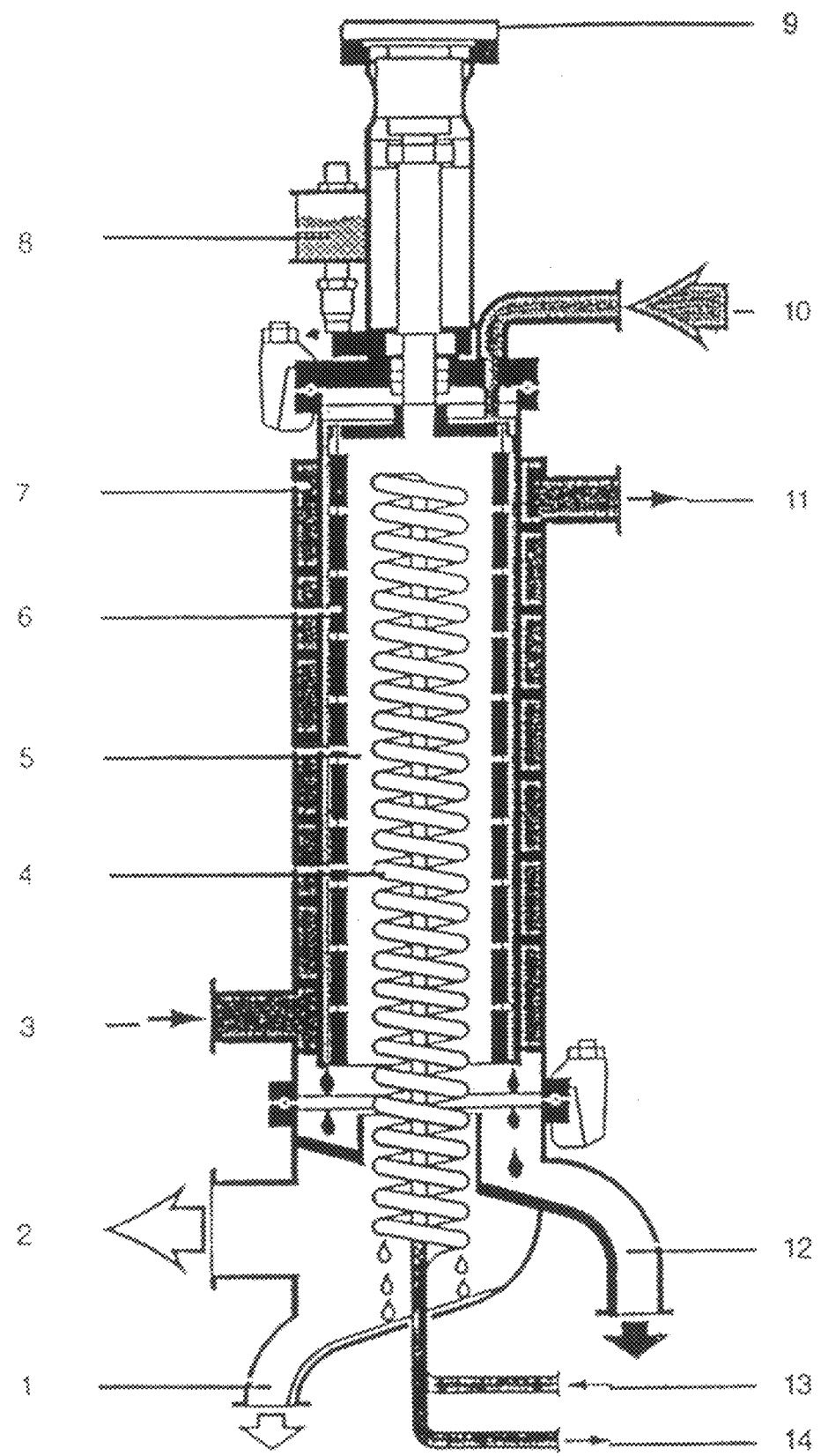
FIG. 1 depicts an apparatus that can be used to carry out a short path distillation in accordance with the present invention.

The process of the invention is particularly useful for separating terbinafine from contaminants, e.g. metal contaminants resulting from its chemical synthesis, e.g. from catalysts, such as copper and/or, in particular, palladium contaminants, particularly for reducing or eliminating contaminants resulting from synthesis in accordance with or similarly to the processes described in e.g. Banyu EP 421302 and/or Dipharma EP 1'236'709, e.g. by reaction of (E)-N-(3-halo-2-propenyl)-N-methyl-N-(1-naphthylmethyl)amine (compound of formula IV of EP 421302 wherein $R^{11}$ is methyl, $R^{21}$ is 1-naphthylmethyl and W is halogen, e.g. bromo, preferably chloro), with 3,3-dimethyl-1-butyne (compound of formula V thereof, wherein $R^7$ is tert-butyl) in the presence of a palladium and/or a copper catalyst to obtain terbinafine base. The catalyst is e.g. copper(I) iodide, or copper(I)iodide together with bis-(triphenylphosphine) palladium-(II)-dichloride or tetrakis(triphenylphosphine)palladium, or a further palladium-, copper- or palladium/copper-containing catalyst selected from those disclosed in EP 421302 A2, e.g. on page 7, line 54 to page 8, line 18.

The process of the invention may be effected by conventional means. It preferably is effected as a so-called "gentle" distillation process. It may e.g. be effected as a batch distillation, or preferably in continuous or semi-continuous manner, and especially as a "short path" distillation, whereby the path between heating mantle and condensor is short, e.g. of the order of 10 cm, thus minimizing the time during which terbinafine is at an elevated temperature, e.g. above 100° C.

The term "short path distillation" is to be understood herewith as a high vacuum distillation to separate mixtures of organic (or silicon) compounds that will not tolerate prolonged heating without excessive structural change or decomposition. It utilizes the heat of condensation as a prime body for radiant heat emission to the surface film of the evaporator. The path between evaporator and condenser is unobstructed. With short residence time and lower distillating temperatures, thermal hazard to the organic material is greatly reduced.

The process of the invention using short path distillation may be effected using commercially available apparatus, e.g. as commercialized by UIC GmbH, D-63755 Alzenau-Hörstein, Germany. A convenient setup is e.g. as illustrated in FIG. 1.

Short path distillation is preferred. It allows short heating time of the mixture which it is intended to purify, as well as cyclical processing, with corresponding improvement in yield of purified product. Further, thickness of the material on the evaporator wall is reduced, allowing lower evaporation temperature and shorter residence time. Very efficient separation from contaminants is achieved thereby, without need for further purification steps such as by chromatography or recrystallization, or using large amounts of charcoal.

Thus, starting from a raw terbinafine base product containing for example from about 10 ppm to about 200 ppm, e.g. about 50 ppm palladium, and/or from about 10 ppm to about 100 ppm, e.g. about 30 ppm copper, one-step short path distillation results in a product containing less than 1 ppm copper, and/or less than 2 ppm palladium as determined using conventional analytical methods such as atom absorption spectroscopy.

Other contaminants, if present, in particular organic compounds, such as (methyl)(naphthalen-1-ylmethyl)amine (by-product 1); 2,2,7,7-tetramethylocta-3,5-diyne (by-product 2); and the Z-isomer of terbinafine, may be eliminated thereby only partially or not at all, e.g. by-product 1 and the Z-isomer of terbinafine.

The invention thus includes i.a.:
a process for the purification of terbinafine which comprises subjecting crude terbinafine in free base form to distillation and recovering the resultant product in free base or acid addition salt form;
a process of the invention which comprises short path distillation;
a process as defined above wherein distillation is effected at a temperature above 100° C. and under reduced pressure;
a process as defined above wherein the crude terbinafine is prepared using a palladium- and/or a copper-containing catalyst;
a process as defined above wherein the purified product contains less than 2 ppm palladium and/or less than 1 ppm copper;
a process as defined above wherein the crude terbinafine contains more than 2 ppm palladium and/or more than 1 ppm copper, and the resultant purified product contains less than 2 ppm palladium and/or less than 1 ppm copper;
a process as defined above wherein at least 5 kg purified product in free base form is prepared per distillation batch or run, preferably at least 50 kg, especially at least 200 kg;
a process as defined above wherein the crude terbinafine in free base form is prepared by reaction of (E)-N-(3-halo-2-propenyl)-N-methyl-N-(1-naphthylmethyl)amine with 3,3-dimethyl-1-butyne in the presence of a palladium and/or a copper catalyst;

purified terbinafine in free base or acid addition salt form whenever prepared by a process as defined above; and terbinafine in free base or acid addition salt form comprising less than 2 ppm palladium and/or less than 1 ppm copper, whenever obtained from a crude product in free base form comprising more than 2 ppm palladium and/or more than 1 ppm copper.

EXPLANATION OF THE FIGURE

Description of FIG. 1

1. Outflow of distillate
2. Connection to vacuum pump
3. Heat inflow
4. Condensor
5. Space under reduced pressure
6. Rolling wipers (distribute crude product evenly to form a film)
7. Heating jacket
8. Sealing liquid, intake
9. Flange for gearing
10. Crude product input
11. Outlet for heat medium
12. Residue outflow
13. Inlet for cooling water
14. Outlet for cooling water The following Examples illustrate the invention. All temperatures are in degrees Centigrade. 1000 mbar=750.06 mmHg; ppm=part per million.

EXAMPLE 1

Batch Distillation (Laboratory Scale)

100 g of crude terbinafine base containing 0.3 area-% of (methyl)(naphthalen-1-ylmethyl)amine (by-product 1) are mixed with 20 g peanut oil and the mixture is heated to 142° at 0.3 mbar pressure (jacket temperature 190°). After 2 hours, 96.4 g of purified terbinafine base as a yellowish distillate and 21.4 g of a dark brown residue are obtained. Due to the thermal impact during batch distillation (2 hours at 142°) the distillate contains about 1 area-% of (methyl)(naphthalen-1-ylmethyl)amine (by-product 1) as determined by gas chromatography (experimental conditions: as for Example 2).

For large scale production the distillation time and the thermal impact would be considerably higher. As a consequence a significantly higher concentration of by-product 1 can be expected unless the distillation time is kept short, such as with e.g. "short path" distillation.

The crude terbinafine base used as a starting material is prepared by reaction of (E)-N-(3-chloro-2-propenyl)-N-methyl-1-naphthalenemethanamine and 3,3-dimethyl-1-butyne in n-butylamine and water in the presence of catalytic amounts of copper(I)iodide and bis-(triphenylphosphine)palladium(II)-dichloride along the lines as described in Example 13 of EP 421302 A2, but without submitting the resultant product to silicagel chromatography.

EXAMPLE 2

Short Path Distillation (Laboratory Scale)

In a commercial thin-film evaporator (from Leybold-Heraeus GmbH, Hanau, Germany: diameter Of heated drum 7 cm; length 25 cm; cooling finger at 50°; pressure 0.2 mbar; Teflon® rotor at 450 rpm) 179 g crude terbinafine base (prepared as described in Example 1 above) are mixed with 8.9 g peanut oil and the mixture is heated to 50°. After evacuation of the whole system to 0.2 mbar, distillation starts by slowly dropping the mixture into the high temperature zone (jacket temperature 160°) where the terbinafine base is heated to the boiling point for only a few seconds. After 2 hours, 171 g (95%) of purified terbinafine base as a yellowish distillate is obtained, which is contaminated with 1 ppm palladium and less than 1 ppm copper. The chemical purity of the distillate is 98.6% terbinafine base (i.e. E-isomer) as determined by gas chromatography (HP-1 column; crosslinked methyl siloxane; length 30 m; film thickness 2.65 μm; column internal diameter 0.53 mm; flame ionization detector (FID) temperature 300°; injector temperature 250°; temperature gradient 50° to 270°; heating rate 20°/min). In addition 10.5 g of distillation residue and 0.4 g of an oily sublimate were obtained. The sublimate consists mainly of 2,2,7,7-tetramethylocta-3,5-diyne (by-product 2).

The overall purity of terbinafine base as determined by gas chromatography is as follows:

|  | Before distillation (crude product) | After distillation (pure product) |
| --- | --- | --- |
| By-product 1 (area-%) | 0.1 | 0.1 |
| by-product 2 (area-%) | 0.7 | 0.2 |
| Z-isomer (area-%) | 0.3 | 0.3 |
| E-isomer (weight-%) | 95.6 | 98.6 |
| Pd (ppm) | 177 | 1 |
| Cu (ppm) | 19 | <1 |

EXAMPLE 3

Short Path Distillation (Industrial Scale)

Distillation of crude terbinafine base is carried out in a fine vacuum distillation apparatus (UIC GmbH KD 150) using short-path distillation with two serial evaporators. Hereby the material is constantly fed and distributed to the inner surface of a vertically oriented evaporator. As the liquid flows downward, an axially arranged roller wiper system distributes this liquid as a thin film which is constantly mixed (see FIGURE). This gentle distillation method therefore reduces both the maximum evaporation temperature and the residence time at high temperature.

The starting temperature values are typically set as follows:
internal limit of feeding tank: 70°;
internal limit of product receiver: 80°; jacket limit of residue tank: 80°;
upper and lower internal limits of evaporators 1 and 2: 100°;
jacket limit of evaporators 1 and 2: 160°.

After control of the whole apparatus for emptiness and cleanliness the maximum vacuum of both evaporators which can be reached by the diffusion pumps is checked:
before and after evaporator 1: $1.6 \times 10^{-1}$ mbar;
before evaporator 2: $2.6 \times 10^{-2}$ mbar;
after evaporator 2: $4.7 \times 10^{-3}$ mbar.

A mixture of 872.5 kg crude terbinafine base (prepared analogously as described in Example 1 above) and 120 kg peanut oil is then transferred to the feeding tank. The peanut oil will ensure that no crusts will build up inside the evaporators. The cooling trap is filled with a mixture of 20 to 30 kg dry ice and about 30 l of ethanol (94%), and temperature values are adjusted as follows:

jacket of the residue receiver: 40';
jacket of evaporator 1: 120°;
condenser of evaporator 1: 50°;
jacket of evaporator 2: 155°;
condenser of evaporator 2: 45°.

The internal temperature of the main receiver is set to 50° as the melting point of the product is around 42°.

When all temperatures are reached the crude product is fed to evaporator 1 with a flow of about 1.5 l/min. The distillate (rest of solvents) of evaporator 1 can be collected in the gauge as its volume is small. The residue of evaporator 1 is transferred to evaporator 2 to distill the crude base, which is collected in the heated main receiver (1.4 l/min) as a yellow liquid.

When all the crude mixture is distilled (around 11 h) the residue of evaporator 2 is transferred to the feeding tank and distilled again. Thereby the jacket temperature of evaporator 1 is reduced to 110° and the jacket temperature of evaporator 2 is reduced to 140°.

After the distillation of the residue is completed (around 2 h) the new residue will be cycled through the evaporators until the flow of the product has reached around 0.2 l/h. Before the cycling can be started the jacket temperature of evaporator 1 is reduced to 100° and the condenser temperature of evaporator 2 is increased to 60°. During the cycling the received distillate becomes darker.

At the end of the distillation (overall about 22.5 h) the apparatus is released with nitrogen. The product from the main receiver is filled at around 50° into drums. A sample is taken and the drums are weighed. The chemical purity of the free base is 97% or higher (here it was 98.4%) as determined by gas chromatography. The yield was 856.1 kg. The amount of copper and/or palladium left was very small or undetectable (less than 1 ppm).

The remaining residue (around 120 kg peanut oil; here it was 128 kg), the distillate of evaporator 1 and the condensates of the cooling traps are combined and incinerated. After five to six batches a cleaning of the apparatus is effected.

COMPARATIVE EXAMPLE

Charcoal Treatment (Laboratory Scale)

To 404 g of a solution of crude terbinafine base in cyclohexane (prepared analogously as described in Example 1 above from 100 g (E)-N-(3-chloro-2-propenyl)-N-methyl-1-naphthalene-methanamine) is added 10 g activated charcoal (Norit Supra®). The mixture is stirred for 17 hours at 20-25° and then filtered. After evaporation of the solvent at reduced pressure 110.5 g (89%) terbinafine base is obtained, which is contaminated with 14 ppm palladium. The chemical purity of the oily residue is 95% as determined by gas chromatography (experimental conditions: as for Example 2).

The invention claimed is:

1. A process for the purification of terbinafine which comprises subjecting crude terbinafine in free base form to distillation at a temperature from about 100° C. to about 170° C., and under a correspondingly reduced pressure, and recovering the resultant purified product in free base or acid addition salt form.

2. A process according to claim 1 which comprises short path distillation.

3. A process according to claim 1 wherein the resultant purified product contains less than 2 ppm palladium and/or less than 1 ppm copper.

4. A process according to claim 3 wherein the resultant purified product contains less than 2 ppm palladium and/or less than 1 ppm copper.

5. A process according to claim 3 wherein the crude terbinafine contains more than 2 ppm palladium and/or more than 1 ppm copper, and the resultant purified product contains less than 2 ppm palladium and/or less than 1 ppm copper.

6. A process according to claim 1 wherein at least 5 kg of the resultant purified product in free base form is prepared per distillation batch or run.

7. A process according to claim 6 wherein at least 50 kg of the resultant purified product is prepared per distillation batch or run.

8. A process according to claim 1 wherein the crude terbinafine in free base form is prepared by reaction of (E)-N-(3-halo-2-propenyl)-N-methyl-N-(1-naphthylmethyl)amine with 3,3-dimethyl-1-butyne in the presence of a palladium and/or a copper catalyst.

9. Purified terbinafine in free base or acid addition salt form that was prepared by a process according to claim 1.

10. A process according to claim 1 wherein crude terbinafine in free base form is subjected to distillation at a temperature from about 110° C. to about 170° C.

* * * * *